United States Patent [19]

Stella et al.

[11] Patent Number: 4,650,803
[45] Date of Patent: Mar. 17, 1987

[54] PRODUCTS OF RAPAMYCIN

[75] Inventors: Valentino J. Stella; Paul E. Kennedy, both of Lawrence, Kans.

[73] Assignee: University of Kansas, Lawrence, Kans.

[21] Appl. No.: 806,152

[22] Filed: Dec. 6, 1985

[51] Int. Cl.⁴ .................. A61K 31/395; C07D 491/06
[52] U.S. Cl. ........................................ 514/291; 546/90
[58] Field of Search ........................... 546/90; 514/291

[56] References Cited

U.S. PATENT DOCUMENTS 4,316,885  2/1982  Rakhit ................................ 514/291

FOREIGN PATENT DOCUMENTS 877700    1/1980   Belgium ............................. 514/291
EP41795  12/1981  European Pat. Off. ............ 514/291

Primary Examiner—Robert T. Bond
Attorney, Agent, or Firm—Arthur G. Seifert

[57] ABSTRACT

Water soluble prodrugs of rapamycin are disclosed which are useful as components in injectable pharmaceutical formulations for the treatment of tumors in mammals.

5 Claims, 1 Drawing Figure

Rapamycin

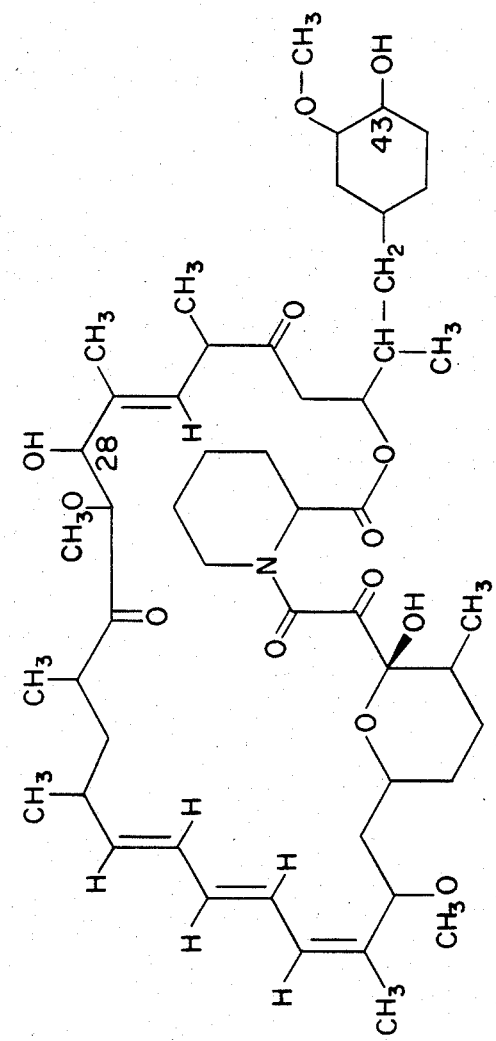

PRODUCTS OF RAPAMYCIN

BACKGROUND OF THE INVENTION

This invention relates to water soluble prodrugs of rapamycin and in particular to certain derivatives of rapamycin such as, for example, the glycinate prodrugs of rapamycin, the propionate prodrugs of rapamycin and the pyrrolidino butyrate prodrugs of rapamycin.

Rapamycin is a known compound described and claimed in U.S. Pat. Nos. 3,929,992, issued Dec. 30, 1975, and 3,993,749 issued Nov. 23, 1976. Morever, certain of its acyl derivatives are disclosed and claimed in U.S. Pat. No. 4,316,885, issued Feb. 23, 1982.

Rapamycin has been disclosed and claimed as useful in the treatment of tumors in Belgian Pat. No. 877,700. Rapamycin is, however, only very slightly soluble in water, i.e. 20 micrograms per milliliter, and special injectable formulations have been developed for administration to patients, such as those described and claimed in European Pat. No. EP 41,795. These formulations are not altogether satisfactory for a number of reasons including toxicity of the carrier. Accordingly, there is a need in the art for a rapamycin derivative or prodrug which is relatively soluble in water so as to form a safe injectable solution and which is as effective as rapamycin in the treatment of tumors.

SUMMARY OF THE INVENTION

It has how been found that water soluble prodrugs of rapamycin can be synthesized which decompose into products including rapamycin in the presence of human plasma and animal tissue homogenates. Such prodrugs of rapamycin provide a component of a valuable pharmaceutical injectable composition for the treatment of tumor in humans.

The water soluble prodrugs of this invention comprise mono-substituted derivatives at position 28 and disubstituted derivatives at positions 28 and 43 of the rapamycin structure. The assignments are based on a structural elucidation published by Findlay et al in Can. J. of Chem. 58, 579 (1980). This structure is reproduced in FIG. 1 of the accompanying drawing.

The mono-substituted derivatives include those having a substituent at position 28 of the rapamycin structure having the following configuration.

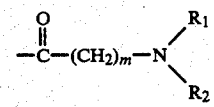

wherein m is an integer from 1 to 3, wherein $R_1$ and $R_2$ are each hydrogen or an alkyl radical having from one to three carbon atoms or wherein $R_1$ and $R_2$ together with the nitrogen atom to which they are attached form a saturated heterocyclic ring having four to five carbon atoms.

The di-substituted derivatives include those having substituents at both positions 28 and 43 of the rapamycin structure having the same configuration as the substituent for the mono-substituted derivative.

DETAILED DESCRIPTION OF THE INVENTION

The preparation of typical water soluble prodrugs of rapamycin of this invention is illustrated in the examples which were carried out using the following procedures.

In the examples, chemical stability studies for rapamycin and the prodrugs were done at 20 μg/ml with an ionic strength of 0.5. Stabilities at pH 3.3 (0.05M acetate buffer) and pH 7.4 (0.05M phosphate buffer) were studied at 25° and 37.5° C. No antioxidants were added and the buffers were not deoxygenated.

The plasma studies were conducted at 37.5° C. for rat and human plasma. Rat plasma was obtained from Sprague-Dawley male albino rats and was used within several days. Human plasma was obtained from the Lawrence Memorial Hospital in Lawrence, Kans. The plasma studies were done at three prodrug concentrations: 200, 100 and 50 μg/ml of prodrug. The experimental procedure was as follows: The compound to be tested was taken from a stock aqueous solution of 5 mg/ml and added to the plasma to give the desired prodrug concentration. Samples of 200 μl were removed at predetermined times and added to 200 μl of 10% metaphosphoric acid to quench the reaction. Before centrifugation 200 μl of methanol was added to further precipitate the plasma proteins. The results are expressed in half-lives in hours.

The chemical and plasma studies were followed by HPLC using a RP C-18 column (150 mm) and a precolumn (50 mm). The mobile phase was 87:13 methanol:phosphate buffer (0.025M, pH 3.4). The detector was set at 254 nm and the flow rate was 1 ml/min for rapamycin studies and 1.5 ml/min for the prodrug studies. Chart speed was 1 inch/10 minutes.

The liver homogenate studies were done using livers freshly obtained from male albino Sprague-Dawley rats. A 20% liver homogenate was prepared in Sorensen's buffer at pH 7.4. Chemical stability studies of rapamycin and the two prodrugs of Examples 2 and 3 were carried out at concentrations of 20, 50 and 50 μg/ml respectively, at 37.5° C.

Rapamycin hydrolysis data in buffers, plasm and in rat liver homogenate are shown in the following table:

TABLE 1

| Chemical Stability Study | | pH | $t_{\frac{1}{2}}$ (hrs) |
|---|---|---|---|
| A. | 25° C. | 3.3 | 35.8 |
| | | 7.4 | 47.6 |
| B. | 37.5° C. | 3.3 | 9.9 |
| | | 7.4 | 10.2 |
| Plasma Stability Study (37.5° C.) | | | |
| | | conc (μg/ml) | $t_{\frac{1}{2}}$ (hrs) |
| A. | Human plasma | 50 | 3 |
| B. | Rat plasma | 50 | 2.83 |
| C. | Liver homogenate | 50 | 5.5 |

In all the prodrug studies, the disappearance of the prodrug peak appeared to result in the formation of a peak with a retention time nearly equal to rapamycin. Analysis of the plasma and homogenate studies by thin layer chromatography (TLC) tended to suggest that rapamycin initially formed but then it further degraded to other decomposition products, as does rapamycin itself in these studies.

EXAMPLE 1

Synthesis of Mono-(28)-N,N-Dimethylglycinate Ester of Rapamycin

In a dry 100 mL round bottom flask was placed 2.80 g ($3.07 \times 10^{-3}$ moles) of rapamycin, 0.616 g ($5.98 \times 10^{-3}$ moles) of N,N-dimethyl glycine and 1.40 g ($6.80 \times 10^{-3}$ moles) of dicyclohexylcarbodiimide. The flask was placed under a nitrogen atmosphere and 60 mL of anhydrous methylene chloride (dried over $P_2O_5$) was added followed by 60 mg of 4-dimethylaminopyridine. The reaction was stirred overnight at room temperature. A thin layer chromatogram (TLC) of the reaction (solvent system 1:1 acetone:methylene chloride) was taken and indicated the reaction to be complete. The Rf of the monoglycinate prodrug was 0.32. Some bisglycinate was also present at a $R_f$ of 0.09. The reaction was worked-up by first filtering off the dicyclohexylurea (DCU). The solvent was removed on the rotovapor to give a white solid. The crude product was chromatographed on 18 gm of silica gel using 300 mL of ethyl acetate to elute rapamycin plus residual DCU. The product was eluted with 1:1 methylene chloride-:acetone to give 1.67 g of product, yield 55%. This material was found difficult to recrystallize. NMR (300 MHZ, solvent $CDCl_3$) indicated the spectrum of the prodrug to be practically identical to that of rapamycin except for the two singlets arising from the glycinate group. The N,N dimethyl protons appeared as a singlet at $\partial 2.32$. The methylene group of the glycinate was found at $\partial 3.16$ as a singlet.

EXAMPLE 2

Synthesis of Methanesulfonic Acid Salt of Mono-(28)-N,N Dimethylglycinate Ester of Rapamycin In a dry 100 mL round bottom flask was placed 3.00 g ($3.10 \times 10^{-3}$ moles) of mono N,N-dimethylglycinate prodrug of rapamycin. This was dissolved in 15 mL of anhydrous methylene chloride (distilled from $P_2O_5$). To this was added $2.71 \times 10^{-3}$ moles) of a stock solution of methanesulfonic acid dissolved in diethyl ether. The solvent was immediately removed to give a white solid, wt. 3.25 g, yield 99%. This compound was also found difficult to recrystallize. The salt form of this compound was found to be unstable to long stirring times. Even in the crystalline form long exposures to light resulted in a slow discoloration of the material.

Data with respect to mono-(28)-N,N-dimethylglycinate methanesulfonic acid salt-prodrug of rapamycin are shown in the following table:

TABLE 2

| Physical Properties | |
|---|---|
| MW | 1095 |
| MP | 93–99° C. |
| Solubility in water | >50 mg/mL |
| HPLC Operating Conditions | |
| Column | RP-18, 150 mm length, 4.6 mm id |
| Precolumn | 50 mm length, 4.6 mm id |
| Mobile phase | 87 parts methanol:13 parts phosphate buffer (0.025 M, pH 3.4) |
| Detector | Kratos 783 UV 254 nm |
| Flow rate | 1.5 mL/min |
| Retention | 9.5 mL* |
| Chemical Stability, 25° C. | |
| Conditions | $t_{\frac{1}{2}}$ (hrs) |

TABLE 2-continued

| | |
|---|---|
| pH 3.3 | 73 |
| pH 7.4 | 45 |
| Plasma/Tissue Stability, 37.5° C. | |
| Conditions | $t_{\frac{1}{2}}$ (hrs) |
| 50 ug prodrug/mL human plasma | 5 |
| 50 ug prodrug/mL rat plasma | 1.8 |
| 50 ug prodrug/mL liver homogenate | 4.5 |

Plasma/Tissue Stability Study (37.5° C.)

| | | conc (μg/ml) | $t_{\frac{1}{2}}$ (hrs) |
|---|---|---|---|
| A. | Human plasma | 200 | 5.6 |
| | | 100 | 4.8 |
| | | 50 | 5.0 |
| B. | Rat plasma | 200 | 2.5 |
| | | 100 | 1.8 |
| | | 50 | 1.75 |
| C. | Liver homogenate | 50 | 4.5 |

*With a new RP C-18 column two peaks were observed which are believed to be cis-trans isomers about the amide bond in the macrocyclic lactone ring.

Reconstitution Procedure

The prodrug can be reconstituted with either water for injection or distilled water containing 5% by weight dextrose (D5W). The solutions should be freshly prepared and used immediately (<1 hr if possible). The prodrug appears to discolor upon prolonged exposure to light. Precaution should be taken to prevent this.

EXAMPLE 3

Synthesis of Mono-(28)-3-(N,N-Diethylamino)propionate Hydrochloride Salt Ester of Rapamycin In a dry 100 mL round bottom flask was placed 1.00 g ($1.09 \times 10^{-3}$ moles) of rapamycin, 0.34 g ($2.16 \times 10^{-3}$ moles) N,N-diethylaminopropionic acid hydrochloride salt and 0.50 g ($2.43 \times 10^{-3}$ moles) of dicyclohexylcarbodiimide.

The vessel was placed under a nitrogen atmosphere and 25 mL of anhydrous methylene chloride (dried over $P_2O_5$) was added followed by 15 mg of 4-dimethylaminopyridine. The reaction was stirred overnight at room temperature. The next day a TLC of the reaction (solvent system: ethyl acetate) on silanized silica gel plate was taken and indicated the reaction to be complete. The $R_f$ of the monopropionate hydrochloride salt of rapamycin was 0.34 and 0.01 for the bispropionate hydrochloride salt which was also formed in the reaction. The dicyclohexylurea was filtered from the reaction and the solvent removed on the rotovapor. The crude product was chromatographed on 12 g of silanized silica gel. The column was first developed with 200 mL of ethyl acetate to remove any rapamycin and also residual dicyclohexylurea. The product was eluted with ethyl acetate to give 0.61 g of product, yield 53%. This compound was found difficult to recrystallize and unstable to prolonged exposure to light. NMR (300 MHz, solvent $CDCL_3$) indicated the spectrum of the prodrug to be practically identical with that of rapamycin. The propionate group did not give sharp easily interpreted resonances as was the case with the glycinate prodrug. This is the result of the resonances being multiplets resulting from the ethyl groups which are not as easily seen among the other resonances from rapamycin. Broad peaks did appear around 1.2 and 1.5 which were not found in rapamycin.

Data with respect to mono-(28)-N,N-diethylaminopropionate hydrochloride salt-prodrug of rapamycin are shown in the following table:

TABLE 3

Physical Properties

| | |
|---|---|
| M.W. | 1077 |
| M.P. | 99–106° C. |
| Solubility | >50 mg/mL in water |

HPLC Operating Conditions

| | |
|---|---|
| Column | RP-18, 150 mm length, 4.6 mm id |
| Precolumn | 50 mm length, 4.6 mm id |
| Mobile phase | 87 parts methanol:13 parts phosphate buffer (0.025 M, pH 3.4) |
| Detector | Kratos 783 UV 254 nm |
| Flow rate | 1.5 mL/min |
| Retention volume | 9.75 mL* |

Chemical Stability

| Conditions | $t_{\frac{1}{2}}$ (hrs) |
|---|---|
| pH 3.3, 25° C. | 33 |
| pH 7.4, 25° C. | 17 |
| pH 3.3, 37.5° C. | 7.9 |
| pH 7.4, 37.5° C. | 6.3 |

Plasma/Tissue Stability, 37.5° C.

| Conditions | $t_{\frac{1}{2}}$ (hrs) |
|---|---|
| 50 ug prodrug/mL human plasma | 2.5 |
| 50 ug prodrug/mL rat plasma | 1 |
| 50 ug prodrug/mL liver homogenate | 3.7 |

Plasma/Tissue Stability Study (37.5° C.)

| | | conc (μg/ml) | $t_{\frac{1}{2}}$ (hrs) |
|---|---|---|---|
| A. | Human plasma | 200 | 3.25 |
| | | 100 | 2.15 |
| | | 50 | 2.50 |
| B. | Rat plasma | 200 | 60 |
| | | 100 | 58 |
| | | 50 | 58 |
| C. | Liver homogenate | 50 | 3.7 |

*Two peaks were also observed for this prodrug when a new RP-18 column was used. This was also believed to be cis-trans isomers as mentioned above for the glycinate prodrug.

Reconstitution Procedure

The prodrug can be reconstituted with either water for injection or D5W. The solutions should be freshly prepared and used immediately (<1 hr if possible). The prodrug appears to discolor upon prolonged exposure to light. Precaution should be taken to prevent this.

EXAMPLE 4

Synthesis of Mono-(28)-4'-(N-pyrrolidino)-butyrate Hydrochloride Salt Ester of Rapamycin In a dry 100 mL round bottom flask was placed 3.50 g ($3.83 \times 10^{-3}$ moles) of rapamycin, 1.48 g ($7.66 \times 10^{-3}$ moles) of 4-pyrrolidino-butyric acid hydrochloride salt and 50 mL of anhydrous methylene chloride (distilled from $P_2O_5$). The reaction was placed under a nitrogen atmosphere and 2.50 g ($1.21 \times 10^{-2}$ moles) of dicyclohexylcarbodiimide and 15 mg of 4-N,N-dimethylaminopyridine. The reaction was stirred overnight at room temperature. The following day the dicyclohexylurea was filtered from the reaction and the filtrate adsorbed onto 5 g of silanized silica gel. This was loaded onto a 12 g column of silanized silica gel and was developed with 75:25 ethyl acetate:hexane to remove the starting material. The product was eluted with ethylacetate to give 3.24 g of a white solid, yield 78%.

Data with respect to the mono-(28)-4'-(pyrrolidino)-butyrate hydrochloride salt-prodrug of rapamycin are shown below:

Physical Properties

| | |
|---|---|
| M.W. | 1088 |
| M.P. | 94–98° C. |
| Solubility | ~15 mg/mL in water |

Reconstitution Procedure

The prodrug can be reconstituted with either water for injection or D5W. The solutions should be freshly prepared and used immediately (<1 hr if possible). The prodrug appears to discolor upon prolonged exposure to light. Precaution should be taken to prevent this.

EXAMPLE 5

Synthesis of Bis N,N-Dimethylglycinate Ester of Rapamycin

The bis-glycinate prodrug of rapamycin substituted at positions 28 and 43 of the rapamycin structure was synthesized by the addition of 1 eq. of rapamycin, 3 eq. of N,N-dimethylglycine, 3.3 eq. of dicyclohexylcarbodiimide and 0.16 eq. of 4-N,N-dimethylaminopyridine. After purification on silica gel, 64% of bis-glycinate was obtained. NMR confirmed the product with two 6 proton singlets for the methyl groups of the two glycinate groups.

The formation of the methane sulfonic acid salt of the bis-glycinate was accomplished by the addition of 1.95 eq. of methane sulfonic acid. The use of two equivalents caused the decomposition of the prodrug. This gave 92% yield of the bis-glycinate prodrug of rapamycin.

The studies carried out using fresh human plasma and fresh rat plasma indicate that the half life of the prodrug of Example 3 was the shortest, i.e. that half of the prodrug decomposed into products including mainly rapamycin within two and one-half hours with rapamycin being the only observed product of hydrolysis.

Similarly as in Example 1, other water soluble derivatives of rapamycin can be prepared using as a reagent instead of N,N-dimethyl glycine, glycine, N,N-diethylglycine, N,N-diisopropylglycine, N-propylglycine, 3-aminopropionic acid, N-ethyl-3-aminopropionic acid, 4-aminobutyric acid, N-ethyl-4-amino butyric acid, N,N-dipropyl-4-aminobutyric acid, 2-(N-pyrrolidino)acetic acid, and 3-(N-piperidino)propionic acid and using appropriate protecting groups where necessary.

What is claimed is:

1. Derivatives of rapamycin which are water soluble and which are mono-substituted derivatives at position 28 and disubstituted derivatives at positions 28 and 43 of rapamycin with the substituents having the configuration:

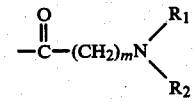

wherein m is an integer from 1 to 3,
wherein $R_1$ and $R_2$ is each hydrogen or an alkyl radical having from one to three carbon atoms or wherein $R_1$ and $R_2$ together with the nitrogen to which they are attached form a saturated heterocyclic ring having four carbon atoms and the pharmaceutically acceptable salts of such derivatives.

2. The mono-substituted derivative of claim 1 wherein the substituent is

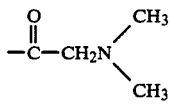

3. The mono-substituted prodrug derivative claim 1 wherein the substituent is

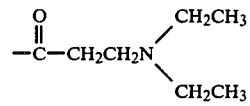

4. The mono-substituted derivative of claim 1 wherein the substituent is

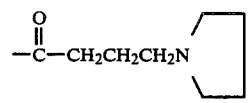

5. An injectable pharmaceutical composition useful in the treatment of tumors comprising a pharmaceutically acceptable carrier and an effective amount of a water soluble derivative of rapamycin as defined in claim 1.

* * * * *

UNITED STATES PATENT AND TRADEMARK OFFICE
CERTIFICATE OF CORRECTION

PATENT NO. : 4,650,803
DATED : March 17, 1987
INVENTOR(S) : Valentino J. Stella and Paul E. Kennedy It is certified that error appears in the above-identified patent and that said Letters Patent are hereby corrected as shown below:

On the Cover Page in Column 1, line 1 after "[54]", amend the title to read:

"PRODRUGS OF RAPAMYCIN"

Signed and Sealed this

Eighth Day of September, 1987

Attest:

DONALD J. QUIGG

Attesting Officer

Commissioner of Patents and Trademarks